United States Patent [19]

Voultoury et al.

[11] Patent Number: 5,683,740
[45] Date of Patent: Nov. 4, 1997

[54] LIPID VESICLES CONTAINING OILY BODIES OF THE SEEDS OF OLEAGINOUS PLANTS

[75] Inventors: Robert Voultoury, Antony; Philippe Flavigny, Boissy Sous Saint Yon, both of France

[73] Assignee: Laboratories de Biologie Vegetale Yves Rocher, La Gacilly, France

[21] Appl. No.: 431,852

[22] Filed: May 1, 1995

[30] Foreign Application Priority Data

May 2, 1994 [FR] France .................. 94 05319

[51] Int. Cl.$^6$ ...................... A23D 7/00
[52] U.S. Cl. ............ 426/633; 426/634; 426/632; 514/844
[58] Field of Search .................. 426/629, 632, 426/633, 634; 514/844, 845, 846, 847, 848

[56] References Cited

U.S. PATENT DOCUMENTS

| | | | |
|---|---|---|---|
| 3,346,390 | 10/1967 | Pichel | 426/630 |
| 3,619,207 | 11/1971 | Dzurik | 426/633 |
| 3,903,311 | 9/1975 | Billerbeck | 426/633 |
| 3,995,068 | 11/1976 | Billerbeck | 426/633 |
| 4,078,361 | 3/1978 | Oberg | 426/629 |
| 4,088,795 | 5/1978 | Goodnight | 426/634 |
| 4,650,857 | 3/1987 | May | 426/632 |
| 4,748,037 | 5/1988 | Matsumoto | 426/634 |
| 4,847,106 | 7/1989 | Pike | 426/629 |
| 4,942,055 | 7/1990 | Avera | 426/633 |
| 5,225,230 | 7/1993 | Seaman | 426/634 |
| 5,230,919 | 7/1993 | Walling | 426/633 |
| 5,240,734 | 8/1993 | Izzo | 426/633 |
| 5,306,513 | 4/1994 | Chablaix | 426/633 |
| 5,436,023 | 7/1995 | Avera | 426/633 |

FOREIGN PATENT DOCUMENTS

WO 91/11169  8/1991  European Pat. Off.

OTHER PUBLICATIONS

Jason T.C. Tzen et al., "Surface Structure and Properties of Plant Seed Oil Bodies", *The Journal of Cell Biology*, vol. 117, No. 2, Apr. 1992, pp. 327–335.

J. Raymond et al. "Les proteines d'oleagineux: proprietes fonctionnelles utilisables en cosmetologie", *Parfums, Cosmetiques, Aromes*, vol. 56, May 1984, p. 57.

*Primary Examiner*—Carolyn Paden
*Attorney, Agent, or Firm*—Young & Thompson

[57] ABSTRACT

Lipid vesicles having an average size of 0.1 to 20 micrometers comprise a covering consisting of practically the whole of the proteins and phospholipids present in the oily bodies of the seeds of oleaginous plants. The covering surrounds a core comprising exogenous lipids and/or exogenous lipophilic substances.

3 Claims, No Drawings

LIPID VESICLES CONTAINING OILY BODIES OF THE SEEDS OF OLEAGINOUS PLANTS

BACKGROUND OF THE INVENTION

1. Field of the Invention

The present invention relates to lipid vesicles and aqueous emulsions containing them, and to a process for producing them.

The present invention relates more specifically to lipid vesicles which comprise as covering the proteins and phospholipids present in the seeds of oleaginous plants.

2. Description of the Related Art

It has been considered hitherto that, in the seeds of oleaginous plants, the oil (essentially triglycerides) was present in the form of oily bodies of average diameter 1 to 10 micrometers, comprising a central core of oil surrounded by a covering consisting of proteins (oleosins) and of phospholipids (J. Tzen et al., J. Cell Bio, 117, 327, 1992).

SUMMARY OF THE INVENTION

It has now been discovered that the proteins constituting the covering of the oily bodies are of two types: some proteins are not glycosylated and other proteins are glycosylated.

The object of the present invention is to provide lipid vesicles which comprise the whole of the proteins and phospholipids present in the covering of the oily bodies, and which hence comprise both unglycosylated proteins and glycosylated proteins identical to those present in the covering of the oily bodies.

Moreover, it is known that, on extraction of the vegetable oils from oleaginous plants, oil cakes are recovered which still contain a substantial fraction of the proteins and phospholipids present in the covering of the oily bodies. These oil cakes contain, in addition, an amount of unextracted oil which can represent from 10 to 30% by weight.

The present invention is directed more specifically towards providing new lipid vesicles and emulsions containing them, while enhancing the value of oil cakes.

To this end, the subject of the present invention is lipid vesicles having an average size of 0.1 to 20 micrometers, in particular 1 to 8 micrometers, and comprising a covering consisting of practically the whole of the proteins and phospholipids present in the oily bodies in the seeds of oleaginous plants, surrounding a core comprising at least some exogenous lipids and/or exogenous lipophilic substances.

The subject of the invention is also an aqueous emulsion comprising lipid vesicles according to the invention dispersed in an aqueous phase.

In the present invention, the expression "practically the whole of the proteins and phospholipids present in the oily bodies of the seeds of oleaginous plants" means that practically the same constituents are to be found in the covering of the vesicles as in the covering of the oily bodies, and that the proteins comprise both unglycosylated proteins and glycosylated proteins. In practice, the proteins and phospholipids present in the seeds of oleaginous plants are those present in oil cakes.

The subject of the invention is also a process for producing such an aqueous emulsion, which comprises:

the grinding of oil cakes, addition of a lipid phase to the ground oil cakes so as to have an overall percentage of lipids of 50 to 95% by weight, kneading of the ground oil cakes and the lipid phase until a homogeneous paste is obtained, in particular at a temperature of 0° to 90° C., addition of an aqueous phase to the paste in a paste/aqueous phase weight ratio of approximately 40:60 to 5:95, in particular at a temperature of 0° to 90° C., stirring of the paste and the aqueous phase to form an emulsion, and, optionally, decantation and/or filtration of the emulsion to remove solid particles, and, optionally, centrifugation of the emulsion to obtain a concentrated emulsion.

DETAILED DESCRIPTION OF THE PREFERRED EMBODIMENTS

As examples of oil cakes, soya bean, pistachio, macadamia, sunflower, rapeseed, groundnut, almond, hazelnut, sesame, borage, wheatgerm and jojoba oil cakes may be mentioned. Oil cakes obtained from seeds having a high oil content (pistachio, macadamia, groundnut, jojoba, hazelnut, almond) are preferably used.

The grinding of the oil cakes may be performed with traditional grinders, such as impeller breakers, advantageously until a particle size of less than 0.1 mm is obtained.

The ground oil cakes may be optionally subjected to an irradiation in order to inactivate bacteria, to an intensity of 10 kGy, and stored under an inert atmosphere in a hermetically sealed packing.

Exogenous lipids denote lipids introduced as supplement, that is to say those which are added and which are not present in the ground oil cakes. These lipids which are added to the ground oil cakes may be lipids of the same type as those present in the oleaginous plants used (endogenous lipids), or other lipids. In general, a relatively large proportion of triglycerides remains in the oil cakes, and lipids are added so as to have an overall percentage of lipids of 50 to 95% by weight.

The amount of lipids is adjusted in accordance with the size of the particles of the final emulsion which it is desired to obtain. Thus, if it is desired to have smaller particle sizes, the amount of lipids added is decreased.

Besides these lipids, it is possible to add lipophilic substances such as vitamins (vitamins D, A, E, K), sunscreen agents (such as Parsol MCX and Parsol 1789 of Givaudan or benzophenone-3), or complex lipophilic mixtures (Titan M262CD of Kemira Oy) to which are optionally added mineral oil, carotene, silicone (for example DC 200 of Dow Corning), fatty esters.

The kneading of the oil cakes and of the added lipid phase is then performed until a homogeneous paste is obtained. It is advantageous to work under a non-oxidizing atmosphere (under vacuum or under nitrogen).

The lipid vesicles can contain from 0.01% to 100% by weight of exogenous lipids or of exogenous lipophilic substances.

The aqueous phase is then added, advantageously at room temperature and under an inert atmosphere (under vacuum or under nitrogen). This aqueous phase can comprise, besides water, various hydrophilic constituents.

The addition of the aqueous phase is generally carried out so as to have a paste/aqueous phase weight ratio of approximately 40:60 to 5:95. A ratio of 30:70 to 5:95 is preferred.

To obtain an emulsion, the whole is subjected to a stirring operation which can be of considerable intensity, for example using a colloid mill.

The emulsion obtained is then optionally subjected to a decantation and/or filtration, for example through a 200-micrometer sieve.

The emulsion obtained is relatively dilute and it is, in general, necessary to concentrate this emulsion by centrifugation. To this end, a disk centrifuge suited to the proportion of the lipid phase may be used. The product obtained is a concentrate of lipid particles in which the proportion of lipophilic components can vary from approximately 20 to 70% by weight, depending on the conditions of production.

Before or after this centrifugation, the lipid suspension can undergo a heat treatment, the conditions of which can vary from 2 seconds to 10 minutes for temperatures of 80° C. to 140° C. A homogenization operation using, for example, a Gaulin type apparatus may then be carried out if desired, which operation can have pressure conditions varying from 5 to $400 \times 10^5$ Pa.

This concentrate of lipid particles may be taken up and diluted with an aqueous phase of the type described below. This aqueous phase may be thickened using gelling agents such as xanthan gum, sclerane gum, bentone and derivatives, cellulose and derivatives, Carbopol and derivatives, carob, carrageenans and derivatives, present at concentrations of 0 to 2% by weight.

The concentrated lipid particles can, in addition, be churned according to dairy techniques to obtain a butter, which is compressed to squeeze out the water therefrom.

The emulsions thereby obtained have, in general, average particle sizes of 0.1 to 20 micrometers.

The emulsions thereby obtained find applications, in particular, in the field of cosmetic products, and the subject of the present invention is also cosmetic compositions comprising lipid vesicles according to the invention (for example hydrating compositions, sun protection compositions, nourishing compositions).

The use in these compositions of a natural emulsifying system (oleosins, phospholipids) leads to better skin tolerance of the final product.

In the case of preparation of an emulsion for cosmetic use, it is possible, for example, to use an aqueous phase comprising:

| | |
|---|---|
| Glycerol | 5 to 10% |
| Propylene glycol | 5 to 10% |
| Butanediol | 5 to 10% |
| Urea | 1 to 5% |
| Sodium PCA | 0.5 to 5% |
| EDTA | 0.05 to 0.1% |
| Methylparaben | 0.05 to 0.2% |
| Propylparaben | 0.05 to 0.1% |
| Butylparaben | 0.05 to 0.1% |
| Ethanol | 0.05 to 0.5% |
| BHT | 0.05 to 1% |
| Sodium alginate | 1 to 5% |
| Vitamin C and derivatives | 0.05 to 1% |
| Vitamin B and derivatives | 0 to 1% |
| Sorbic acid | 0 to 1% |
| Various aqueous preparations of trace elements | |
| Sodium sulphite | 0 to 4% |

The emulsions according to the invention also find applications in the field of food products. The subject of the present invention is hence also food compositions comprising lipid vesicles according to the invention. As an example, cholesterol-free vitaminized milk-type supplements, milk-type fermented desserts, yoghurts and whipped creams may be mentioned. The milk-type fermented desserts and the yoghurts may be produced by adding lactobaccillus strains to an emulsion according to the invention, followed by incubation for 5 hours at approximately 35° C. The whipped creams may be obtained by adding 90 parts of a propellant ($CO_2$ or $N_2O$) to 10 parts of a concentrated emulsion according to the invention, to which customary food additives (flavourings and sugars) are added.

The emulsions according to the invention also find applications in the field of pharmaceutical products for human or veterinary use, in conjunction with the intrinsic properties of the oleosins (small size and lipophilic character).

Thus the subject of the present invention is also pharmaceutical compositions. As an example, compositions for supplying vitamin E, vitamins D or hormones via transdermal patches may be mentioned.

In addition, it should be noted that the emulsions obtained comprise proteins which display a great similarity to the apolipoproteins of mammals; in other words, the lipases of mammals are thought to recognize the proteins of the emulsions according to the invention, enabling the lipases to be bound to the membranes of the particles, and consequently the lipids which are substrates of the lipases in question to be degraded.

The examples which follow illustrate the present invention.

EXAMPLE 1

A groundnut oil cake is ground using an impeller breaker until a size of less than approximately 0.1 mm is obtained.

The oil cake contains approximately 20% by weight of triglycerides.

50 parts of vegetable oil (groundnut triglycerides or those of some other oleaginous plant) are added to 50 parts of ground oil cake. The whole is kneaded under vacuum at room temperature until a homogeneous paste is obtained.

900 parts of water are added to this paste. The whole is subjected at room temperature and under vacuum to vigorous stirring using a colloid mill turned to the maximum setting.

The product is filtered through a 200-micrometer sieve. The filtrate, which is a very fluid milk, is optionally centrifuged in a dairy centrifuge.

A concentrate of lipid particles having an average size of 3 micrometers, containing approximately 60% of triglycerides, is obtained.

EXAMPLE 2

The procedure is as in Example 1, with a macadamia oil cake (containing 25% by weight of triglycerides), adding 70 parts by weight of triglycerides (macadamia oil or that of other oleaginous plants) to 30 parts by weight of oil cake.

Water is added to the paste in the proportion of 900 parts by weight.

A concentrate of lipid particles having an average size of 3 micrometers is finally obtained, this concentrate containing approximately 60% of triglycerides.

Examples of compositions obtained according to the process of the invention are given below.

Example A—Face Milk

| | |
|---|---|
| Water | qs. 100% |
| Xanthan gum | 1 to 2% |

| | |
|---|---|
| Concentrate A | 20 to 40% |
| Perfume | 0.1 to 0.5% |
| Preservatives | qs |

The concentrate A is produced as described in Example 1, from a vegetable oil.

The pH varies from 5.5 to 6.5 (qs=citric acid). Viscosity 2000 to 3000 cP.

Example B—Total Sun Block Milk

| | |
|---|---|
| Water | qs 100% |
| Xanthan gum | 1 to 2% |
| Concentrate B | 20 to 40% |
| Perfume | 0.1 to 0.5% |
| Preservatives | qs |

The concentrate B is produced as described in Example 1, from an oil composed, for example, of:

| | |
|---|---|
| Tryglycerides | qs 100% |
| PARSOL 1789 | 1 to 5% |
| PARSOL MCX | 1 to 15% |
| TITAN M262CD | 1 to 10% |

The pH varies from 5.5 to 6.5 (qs=citric acid). The viscosity 2000 to 3000 cP.

Example C—Hydrating Body Milk

| | |
|---|---|
| Water | qs. 100% |
| Glycerol | 5 to 10% |
| Xanthan gum | 1 to 2% |
| Urea | 1 to 5% |
| Concentrate C | 20 to 40% |
| Perfume | 0.1 to 0.5% |
| Preservative | qs |

The concentrate C is produced as described in Example 1, from vegetable oil to which jojoba fatty esters (5 to 10%) are added.

The pH varies from 6.0 to 6.5 (qs=citric acid), the viscosity from 2000 to 3000 cP.

Example D—Cholesterol-free Vitaminized Milk-type Supplement

| | |
|---|---|
| Water | qs. 100% |
| Vitamin C | 1% |
| Xanthan gum | 0.5 to 1% |
| Concentrate D | 20 to 40% |
| Vanilla extract | qs |
| Preservatives | qs |

The concentrate D is produced as described in Example 1, using oil having a high content of gamma-linolenic triglycerides and to which vitamin D (500 IU/g max) or A (1500 IU/g max) is added.

The preservatives may be left out if the following conditions are adopted:

initial inactivation of bacteria in the oil cake,

UHT treatment (120° C.×3 seconds) of the suspension, before or after the additions described, storage in Tetrapak or equivalent, otherwise food preservatives will be chosen, and preferably:

sorbic acid various parabens sodium sulphite

BHT the pH will be adjusted to 6.5±0.2 using citric acid.

Results of tests revealing the different natures of the proteins present in the covering of the oily bodies are given below.

EXAMPLE 3

The procedure was as in Example 2, starting from a macadamia oil cake.

From a concentrate of lipid vesicles, the proteins were separated by the method employing urea gradients after extraction of the lipids with diethyl ether (Millichip, Int. Colloquium Plant Lipids).

The proteins were redissolved in 10 mM Tris-HCl buffer, 0.07M SDS, pH 8.

Purification of the proteins was carried out by molecular sieve chromatography on a Superose 6 column equilibrated and eluted in 10 mM Tris-HCl buffer, 0.07M SDS, pH 8.2.

50 fractions were separated, and fractions 7, 36 and 43 corresponding to elution peaks were tested. To this end, a "dot-blot" type technique was used, with a serum directed against soya bean β-glucosidase which reacts with the complex carbohydrate units common to most plants, which contain $(1 \to 3)$-α-glucose and $(1 \to 2)$-β-xylose residue.

Fractions 7 and 36 are recognized by serum directed against β-glucosidase, which is not the case as regards fraction 43. The recognition is hence attributable to the presence of glycoside chains in fractions 7 and 36 which do not occur in the case of fraction 43.

We claim:

1. Cosmetic composition comprising an effective amount of lipid vesicles in a cosmetic base, said lipid vesicles having an average size of 0.1 to 20 micrometers and comprising a covering consisting of practically the whole of the proteins and phospholipids present in the oily bodies of the seeds of oleaginous plants, surrounding a core comprising at least one of exogenous lipids and exogenous lipophilic substances.

2. Cosmetic composition comprising an effective amount of lipid vesicles having an average of 0.1 to 20 micrometers and consisting essentially of a covering consisting of practically the whole of the proteins and phospholipids present in the oily bodies of the seeds of oleaginous plants, surrounding a core consisting essentially of substances selected from exogenous lipids, exogenous lipophilic substances and mixtures thereof, in a cosmetic base.

3. Lipid vesicles having an average of 0.1 to 20 micrometers and consisting essentially of a covering consisting of practically the whole of the proteins and phospholipids present in the oily bodies of the seeds of oleaginous plants, surrounding a core consisting essentially of substances selected from exogenous lipids, exogenous lipophilic substances and mixtures thereof, wherein the proteins and phospholipids are those present in oil cakes.

* * * * *